April 29, 1941. F. H. HOWARD Plant Pat. 464
ROSE PLANT
Filed Nov. 18, 1940
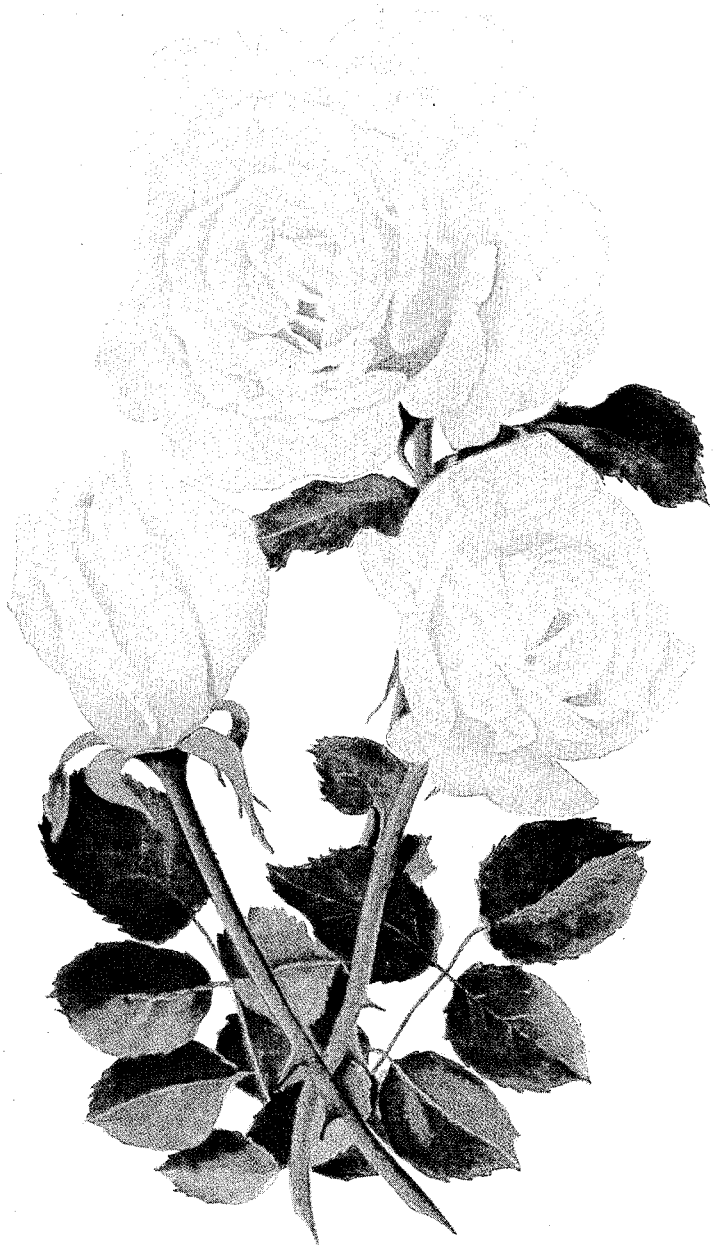
INVENTOR
Frederick Huber Howard
By Orville M. Kile
Plant Pat. Agt.

Patented Apr. 29, 1941

Plant Pat. 464

UNITED STATES PATENT OFFICE

464

ROSE PLANT

Frederick Huber Howard, Montebello, Calif.

Application November 18, 1940, Serial No. 366,186

1 Claim. (Cl. 47—61)

This new variety is a cross of the Mrs. J. D. Eisele by Glowing Sunset. It has been asexually reproduced and has retained its principal characteristics, notably perfection of form of its bud and blossom, its distinctive color and its strong growth.

The original illustrations accompanying this application show three specimens of the blossoms of this new variety in various stages of opening, together with stems and foliage. These are shown in as nearly their true form and colors as the artist was able to make them.

Following is a detailed description of this new rose variety. Color reference is to Ridgway's Color Standards and Nomenclature except where obviously the ordinary dictionary term is intended.

*The plant*

Growth: Very vigorous and bushy.

Blooming habit: Continuous; very free blooming.

Disease resistance: Apparently free from the usual rose diseases.

Foliage: Healthy and abundant; unusually handsome; 3 to 5 leaflets.

*Leaflets.*—Medium in size, terminal leaflet averaging about 1½ inches by 2 inches. *Shape*—oval. *Color*—Dark Dull Yellow Green (Plate XXXII), but with a glossy surface. Under surface much lighter. *Edge*—sharply and finely serrated. *Texture*—substantial and leathery. *Appearance*—glossy and deep veined.

Stems: Very stiff and strong; Cerro Green (Plate V) with heavy overlay of Neutral Red (Plate XXXVIII).

Thorns: Many; large; sharp; downward-pointing.

Rachis: Heavy; smooth below; grooved above.

Stipules: Long; medium width; points long.

*The flower*

Bud:

*Size.*—Medium.

*Shape.*—Long-pointed; later opens into modified urn-shape, edges of its petals being wavy and notched. Perfectly formed.

*Peduncle.*—Short; cover with small spines; usually has deep reddish overlay.

*Color.*—Tip is Peach Red to Geranium Pink (Plate I), merging into Peach Red (Plate I) suffused with Capucine Orange (Plate III) in central part of petal.

*Sepals.*—Simple; broad.

Blossom:

*Size.*—Large, 4 to 4½ inches across.

*Form.*—Loose; high-centered; with petals irregular and wavy.

*Petalage.*—Double, approximately 43 petals in the month of June in my gardens.

*Fragrance.*—Moderate.

*Color.*—The partly opened blossom shows the inner surface of the petals to be Strawberry Pink to Geranium Pink (Plate I) on the outer edge, merging into Grenadine (Plate II) to Capucine Orange (Plate III) at the base. The central petals which show their outer surfaces at this stage are strongly suffused with the Capucine Orange (Plate III). The outer surface of the petals is a deeper shade of the same general colors. When the blossoms are fully open so that the stamens show, the colors take on a lighter tint, but retain their general tonality.

Petals:

*Shape.*—Outer petals obovate; inner petals much narrower.

*Margin.*—Wavy and notched; rolls back gradually.

*Size.*—Outer petals average 2¼ by 1¾ inches. Inner petals smaller.

*Texture.*—Substantial.

*Appearance.*—Silky.

*Arrangement.*—Regular, but the open blossoms have a somewhat ragged appearance.

*Behavior.*—Clinging.

Longevity: Lasts well both on the plant and as a cut flower.

Reproductive organs:

*Pistils.*—Many; tightly bunched. *Styles*—Short. *Stigmas*—Light yellow with slight tinge of red.

*Stamens.*—Many; surround pistils. *Filaments*—of varying lengths; curved; slender; Empire Yellow (Plate IV). *Anthers*—Light Cadmium (Plate IV); medium in size.

Having thus disclosed my invention, I claim:

The new and distinct variety of hybrid tea rose plant herein shown and described, characterized particularly by its strong growth; its handsome, leathery foliage; its bud of good, long-pointed form; and its blossoms having a loose, high-centered form and petals with wavy and notched edges and a distinctive combination of colors from Geranium Pink to Capucine Orange.

FREDERICK HUBER HOWARD.